United States Patent
Lurie (10) Patent No.: US 12,213,845 B2
(45) Date of Patent: Feb. 4, 2025

(54) ULTRASOUND GUIDED FEMORAL ARTERY ACCESS SYSTEM (UFAAS) AND METHOD TO ENHANCE BRAIN PERFUSION DURING NEUROPROTECTIVE CPR

(71) Applicant: VitalinC LLC, Minneapolis, MN (US)

(72) Inventor: Keith G. Lurie, Minneapolis, MN (US)

(73) Assignee: Resuscitation Innovations LLC, Minneapolis, MN (US)

( * ) Notice: Subject to any disclaimer, the term of this patent is extended or adjusted under 35 U.S.C. 154(b) by 0 days.

(21) Appl. No.: 18/501,913

(22) Filed: Nov. 3, 2023

(65) Prior Publication Data
US 2024/0148465 A1 May 9, 2024

Related U.S. Application Data

(60) Provisional application No. 63/382,231, filed on Nov. 3, 2022.

(51) Int. Cl.
*A61H 31/00* (2006.01)
*A61B 90/00* (2016.01)

(52) U.S. Cl.
CPC ........... *A61B 90/37* (2016.02); *A61H 31/007* (2013.01); *A61B 2090/378* (2016.02)

(58) Field of Classification Search
CPC ... A61B 8/4455; A61B 8/4483; A61B 8/4494; A61B 8/488; A61B 8/5207; A61B 8/56; A61B 1/00009; A61B 1/00045; A61B 1/0005; A61B 1/00103; A61B 1/00105; A61B 1/00144; A61B 1/00147; A61B 1/0052; A61B 1/0057; A61B 1/015; A61B 1/05; A61B 1/307; A61B 10/0233; A61B 2090/378; A61B 8/0841; A61B 8/12; A61B 8/4416; A61B 8/4427; A61B 8/445; A61B 8/4461; A61B 8/463; A61B 8/483; A61B 8/5215; A61B 8/54; A61B 90/11

See application file for complete search history.

(56) References Cited

U.S. PATENT DOCUMENTS

| | | | |
|---|---|---|---|
| 9,707,152 | B2 | 7/2017 | Lurie et al. |
| 9,750,661 | B2 | 9/2017 | Lurie et al. |
| 9,801,782 | B2 | 10/2017 | Lurie et al. |
| 10,092,481 | B2 | 10/2018 | Lurie |
| 10,245,209 | B2 | 4/2019 | Lurie |
| 10,350,137 | B2 | 7/2019 | Lurie et al. |

(Continued)

OTHER PUBLICATIONS

PCT/US2023/078725, "Invitation to Pay Additional Fees and, Where Applicable, Protest Fee", Feb. 23, 2024, 2 pages.

(Continued)

*Primary Examiner* — Jon Eric C Morales
(74) *Attorney, Agent, or Firm* — Kilpatrick Townsend & Stockton LLP (57) ABSTRACT

A handheld ultrasound guiding system for the transcutaneous delivery of a needle into blood vessel that can be used to then deliver a guidewire, the battery powered light-weight device consisting of a phased array ultrasound generator, a transducer probe, a screen, computer processor that is mechanically coupled to a needle holder mounted at an angle to the ultrasound probe, the needle is mounted such that it can be advanced into a target blood vessel that is being visualized real-time by the ultrasound probe.

16 Claims, 8 Drawing Sheets

(56) References Cited

U.S. PATENT DOCUMENTS

| | | |
|---|---|---|
| 10,406,068 B2 | 9/2019 | Lurie et al. |
| 10,406,069 B2 | 9/2019 | Lurie et al. |
| 10,667,987 B2 | 6/2020 | Lurie |
| 11,020,314 B2 | 6/2021 | Lurie |
| 11,096,861 B2 | 8/2021 | Lurie |
| 11,246,794 B2 | 2/2022 | Lurie |
| 11,259,988 B2 | 3/2022 | Lurie et al. |
| 2003/0233046 A1 | 12/2003 | Ferguson et al. |
| 2014/0048061 A1 | 2/2014 | Yannopoulos et al. |
| 2014/0073910 A1 | 3/2014 | Munrow et al. |
| 2014/0363391 A1 | 12/2014 | Yannopoulos et al. |
| 2019/0159963 A1 | 5/2019 | Lurie |
| 2020/0230391 A1 | 7/2020 | Burkholz et al. |
| 2021/0000685 A1 | 1/2021 | Lurie |
| 2021/0308007 A1* | 10/2021 | Lurie .................. A61H 31/006 |
| 2021/0322264 A1 | 10/2021 | Lurie |
| 2022/0061806 A1 | 3/2022 | Burkholz |
| 2022/0265508 A1 | 8/2022 | Lurie et al. |
| 2022/0313211 A1 | 10/2022 | Eltorai et al. |

OTHER PUBLICATIONS

PCT/US2023/078725, "International Search Report and Written Opinion", Apr. 19, 2024, 13 pages.

\* cited by examiner

ULTRASOUND GUIDED FEMORAL ARTERY ACCESS SYSTEM (UFAAS) AND METHOD TO ENHANCE BRAIN PERFUSION DURING NEUROPROTECTIVE CPR

CROSS-REFERENCE TO RELATED APPLICATION

This application claims benefit of U.S. Provisional Patent Application No. 63/382,231, entitled, "ULTRASOUND GUIDED FEMORAL ARTERY ACCESS SYSTEM (UFAAS) AND METHOD TO ENHANCE BRAIN PERFUSION DURING NEUROPROTECTIVE CPR", filed Nov. 3, 2022, the contents of which are hereby incorporated by reference in their entirety.

BACKGROUND OF THE INVENTION

Ultrasound is widely used to identify vascular structures, including arteries and veins for various medical tests and/or procedures, and in particular, procedures such as Resuscitative Endovascular Balloon Occlusion of the Aorta (REBOA) in which a catheter is inserted into an artery. Conventionally an ultrasound probe containing one or more sensors may be positioned against a patient to produce an ultrasound image that may be viewed on a screen. There are a wide range of sizes and shapes for the ultrasound probes, which are generally hand-held, and the ultrasound machine, which is used to generate and generally display the ultrasound image. One such machine, the Butterfly (US201461981491P) is a pocket-size hand-held that can be used to easily image the femoral artery. When ultrasound-guided vascular access is used, a probe is often held by the operator in one hand and the needle is held in the other hand. Once the needle is inserted into the vessel, typically the operator may either let go of the needle while finding and then inserting a guide wire through the needle or the operator may let go of the ultrasound probe to stabilize the needle. Both approaches can work but can result in small movement of the needle which results in loss of access and the inability to thread wire and ultimately cannulate the vessel. Such approaches may be difficult or impractical when pulsations of the veins and/or arteries occur and/or when time is of the essence this approach can result in worse clinical outcomes. For example, ultrasound visualization to implant a REBOA catheter, an operator can see real-time images of both the femoral artery and immediately adjacent vein, but vibrations can result in movement of the small insertion needle that is used to initially cannulate the artery. This can reduce the success rate of cannulation and thus reduce the benefit of REBOA. Therefore, improvements in ultrasound techniques for transcutaneous vascular access are desired.

SUMMARY OF THE CLAIMS

A handheld ultrasound guiding system for the transcutaneous delivery of a medical implement into a vascular access structure may include a body. The system may include an ultrasound probe coupled with a first end of the body. The system may include a display device coupled with a second end of the body. The display device may be configured to present an image generated using the ultrasound probe.

In some embodiments, the system may include a needle-positioning member coupled with the body. The needle-positioning member may define a needle channel. The needle channel may be alignable with an imaging axis of the ultrasound probe. The needle-positioning member may be detachably coupled with the body. An angle of the needle-positioning member may be adjustable relative to the body. The needle-positioning member may be retractable into the body. The display device and the ultrasound probe may be battery powered. The display device may be detachably coupled with the body. A total length of the body may be between 4 inches and 15 inches.

Some embodiments of the present technology may encompass methods of performing cardiovascular resuscitation. The methods may include elevating an individual's head, shoulders, and heart relative to the individual's lower body while the individual's lower body remains generally aligned with a horizontal plane. The methods may include compressing the individual's chest while the individual's head, shoulders, and heart are elevated. The methods may include regulating an intrathoracic pressure of the individual while the individual's head, shoulders, and heart are elevated relative to the lower body. The methods may include performing REBOA on the individual.

In some embodiments, performing REBOA may include positioning an intra-aortic balloon in the individual's aorta using an ultrasound-guided cannulation device and inflating the intra-aortic balloon. The methods may include performing active compression decompression cardiopulmonary resuscitation on the individual while the individual is in a supine position in general alignment with the horizontal plane prior to elevating the individual's head, shoulders, and heart. The methods may include actively decompressing the individual's chest between each chest compression. Regulating the intrathoracic pressure may include interfacing an impedance threshold device with the individual's airway. Elevating the individual's head, shoulders, and heart may include elevating the individuals' head to a height of between 10 cm and 30 cm above the horizontal plane and elevating the individual's heart to a height of between 5 cm to 15 cm above the horizontal plane. REBOA may be performed on the individual while the individual's head, shoulders, and heart are elevated.

Some embodiments of the present technology may encompass methods for cannulating a vascular access structure. The methods may include maneuvering an ultrasound probe coupled with a body of a cannulation device over an individual's body. The methods may include locating a vascular access structure of the individual based on an image presented on a display device coupled with the body of the cannulation device. The image may be generated based on signals from the ultrasound probe. The methods may include inserting a medical implement into the vascular access structure.

In some embodiments, the medical implement may include a hollow needle. Inserting the medical implement into the vascular access structure may include aligning the hollow needle with the vascular access structure using a needle-positioning member of the body that holds the hollow needle into alignment with an imaging axis of the ultrasound probe. The methods may include advancing a guidewire through a hollow bore of the hollow needle and into the vascular access structure under ultrasound visualization. The methods may include retracting the hollow needle into a sheath prior to advancing the guidewire. The methods may include adjusting an orientation of the display device relative to the body.

BRIEF DESCRIPTION OF THE DRAWINGS

A further understanding of the nature and advantages of the disclosed technology may be realized by reference to the remaining portions of the specification and the drawings.

Several of the figures are included as schematics. It is to be understood that the figures are for illustrative purposes, and are not to be considered of scale or proportion unless specifically stated to be of scale or proportion. Additionally, as schematics, the figures are provided to aid comprehension and may not include all aspects or information compared to realistic representations, and may include exaggerated material for illustrative purposes.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the letter.

DETAILED DESCRIPTION OF THE INVENTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Outcomes with conventional cardiopulmonary resuscitation (CPR) are generally dismal, especially in out-of-hospital cardiac arrest patients. For example, in 2021 and 2022 only 7.4% of out-of-hospital cardiac arrest patients in the USA survived with favorable brain function. This is often due to lack of timely treatment and/or treatment using techniques that do not generate sufficient levels of cerebral perfusion pressure to adequately deliver oxygenated blood to the brain. Embodiments of the present invention are directed to devices and methods to improve outcomes after cardiac arrest when CPR is needed. In particular, embodiments may enable new methods that markedly improve brain perfusion during CPR, such as by performing Neuroprotective CPR, (defined herein as the combination of active compression and decompression of the chest, an impedance threshold device, and controlled gradual elevation of the head and thorax), in combination with ultrasound-guided delivery and deployment of a Resuscitative Endovascular Balloon Occlusion of the Aorta (REBOA) catheter. This sequential method of resuscitation provides a novel means to achieve markedly higher brain blood flow during CPR. In particular, while Neuroprotective CPR results in near normal cerebral perfusion pressures, higher brain blood flow, and a higher likelihood of survival after cardiac arrest, additional hemodynamic support can be particularly of benefit, especially during prolonged resuscitation efforts that last more than 20 minutes. The REBOA occludes the aorta to limit arterial blood flow distal to the occlusion balloon, and restricts the effective circulating vascular volume to a region above the occlusion, thereby increasing compression and decompression phase arterial pressures proximal to the occlusion. This results in unexpectedly higher cerebral perfusion pressures and coronary perfusion when used in conjunction with Neuroprotective CPR.

Performing Neuroprotective CPR in conjunction with REBOA may require specialized equipment and devices, including an ultrasound-guided femoral artery cannulation device. During REBOA, the femoral artery is often used as a catheterization access point. For example, femoral artery catheterization is used during coronary angiography, for arterial blood pressure monitoring, and for blood sampling. Access to the femoral artery is generally performed in a 'blinded' manner, by feeling for a pulse and then inserting a needle into the femoral artery, at times the pulse may be absent, difficult to feel, or difficult to identify, especially on patients exhibiting low blood pressure, during cardiac arrest, and/or during the performance of CPR. Additionally, in the setting of a cardiac arrest, when it may be of benefit to insert a REBOA catheter, motion associated with delivery of CPR can result pulsations of both the femoral artery and adjacent vein that may make it difficult to successfully cannulate the femoral artery. The ability to access the femoral artery may be further compromised when treating patients in out-of-hospital environments, as conventional imaging devices to visualize the artery may not be available, even in ambulances and/or smaller medical facilities. Moreover, oftentimes, non-hospital staff (e.g., paramedics, clinicians, etc.) are not properly trained in how to access the femoral artery for delivery of the occlusion device. Such issues make it even more difficult to implement REBOA in out-of-hospital treatment settings.

To further improve outcomes, a means to selectively and rapidly insert an aortic balloon occlusion catheter may be utilized in conjunction with Neuroprotective CPR. For example, embodiments of the present technology may include femoral artery catheterization devices that use ultrasound imaging to visualize and locate the femoral artery. The devices may include a needle holder and insertion system to assist in advancing a needle into the femoral artery and stabilizing the needle thereafter with on-going real time direct ultrasound visualization. By integrating an ultrasound probe and needle holder into a single device, the femoral artery catheterization devices and cannulation methods described herein may provide a safer, quicker, and more effective way to cannulate the femoral artery and other arteries and veins during Neuroprotective CPR, or as part of any other medical procedure. Such devices may help properly cannulate the femoral artery, even in the presence of vibrations or other movements from the performance of CPR that may result in movement of the small insertion needle that is used to initially cannulate the artery, thereby improving the success rate of cannulation. While disclosed primarily in the context of REBOA cannulation during Neuroprotective CPR, it will be appreciated that the cannulation techniques disclosed herein are not so limited. The cannulation devices and techniques described herein may be used to cannulate the femoral artery, and other vascular access structures (e.g., brachial artery, radial artery, carotid artery, jugular vein, and femoral vein) for any number of medical procedures. As such, it will be appreciated that the catheterization devices that use ultrasound imaging, including the cannula devices and techniques described herein, are not intended to be limited solely for use with CPR, but may be used with various other procedures as well.

In some embodiments, the Neuroprotective CPR+REBOA may be performed using existing CPR devices and methods that combine active compression and decompression of the chest, an impedance threshold device, and a means and structure for controlled gradual elevation of the head and thorax. Such CPR devices and methods may include those described herein, as well as those described in U.S. application Ser. No. 17/668,266, U.S. application Ser. No. 17/335,922, U.S. application Ser. No. 17/222,476, U.S. application Ser. No. 16/955,382, U.S. application Ser. No. 16/201,339, U.S. Pat. Nos. 11,259,988, 11,246,794, 11,096,861, 11,020,314, 10,667,987, 10,406,069, 10,406,068, 10,350,137, 9,801,782, 9,750,661, 9,707,152, 10,092,481, and 10,245,209, the complete disclosures of which have previously been incorporated by reference for all intents and purposes.

Figure 1:
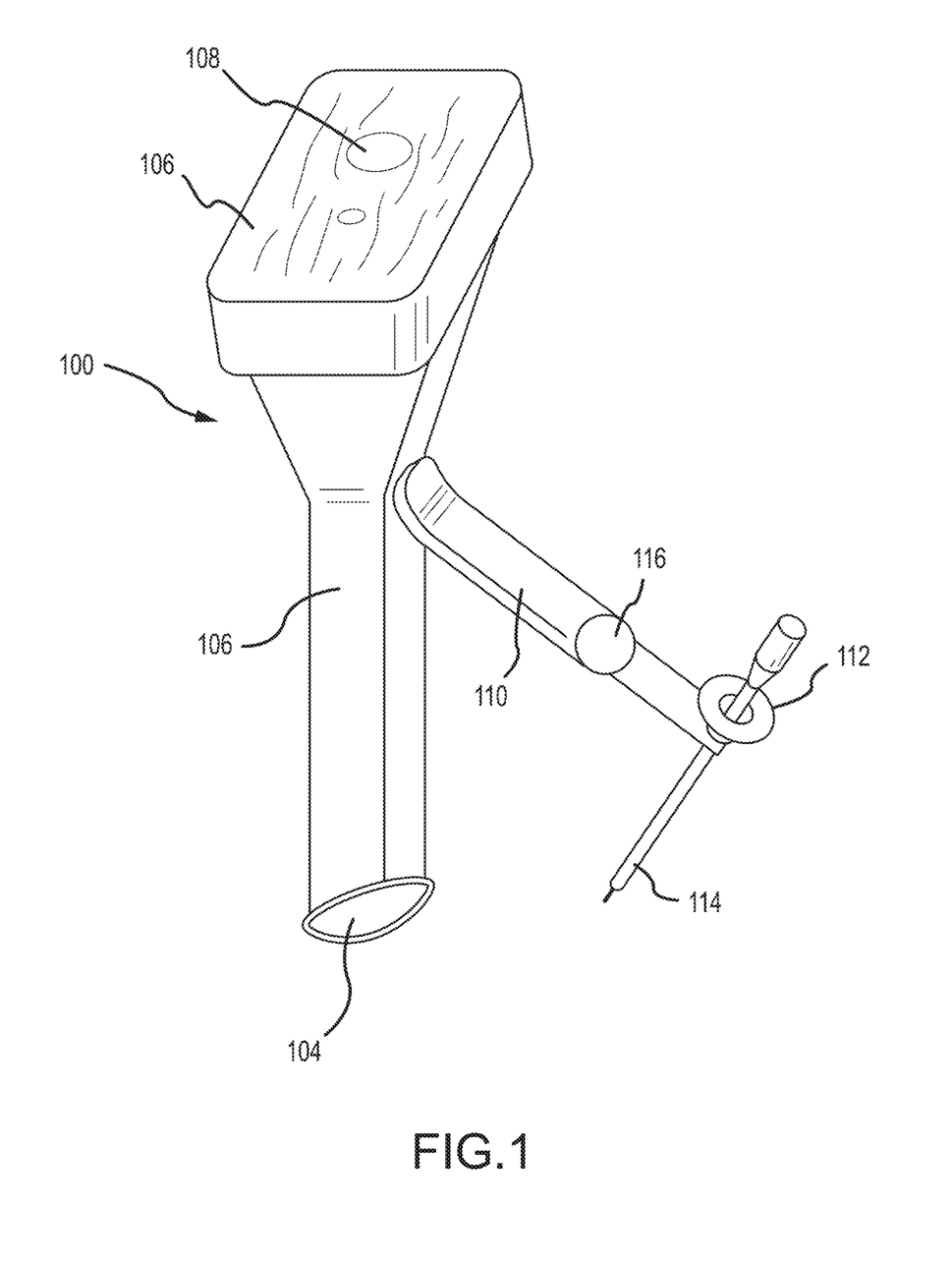
FIG. 1 illustrates a handheld cannulation device according to embodiments of the present technology.

Turning now to FIG. 1, one embodiment of an ultrasound-guided cannulation device 100 is illustrated. The cannulation device 100 may be in the form of a handheld device that may enable an operator to use ultrasound to visually locate and subsequently cannulate (or otherwise access) a desired vascular access structure. The cannulation device 100 may include an elongate body 102 that may be sized and shaped to be graspable using a single hand. In some embodiments, the body 102 may have a substantially constant cross-section along a length of the body 102, while in other embodiments the body 102 may have a variable cross-section along the length. For example, as illustrated, the body 102 tapers from a patient interface end 104 to a display end 106. Other profiles (e.g., stepped, angled, curved, etc.) may be used in various embodiments.

The body 102 may include all necessary components to generate and view an ultrasound image. For example, the body 102 may house a battery or other power source, one or more processors, circuits, ultrasonic transducers, display screens, etc. In other words, the entire ultrasound device including the screen, probe, power supply, and hardware and software are a single unit. This may enable an operator to view an ultrasound image and the cannulation device 100 simultaneously, which may help facilitate improved cannulation of a vascular access structure as will be described below. The patient interface end 104 may be or include a probe tip that includes one or more ultrasonic transducers that may transmit high frequency sound waves (e.g., >20 kHz) to the body and record reflected or echo waves. An image processor disposed within the body 102 may use the recorded waves to develop 2-D real-time images. The image processor may also be disposed in other parts of the device. These images may be displayed, in real-time, using a display screen 108 that is integrated into the display end 106 of the body 102. For example, in a particular embodiment, the display screen 108 may be positioned on an opposite end surface as the probe and/or ultrasonic transducer. In some embodiments, the display screen 108 may include a touchscreen and/or may be electrically coupled with one or more buttons and/or other user interface inputs that enable an operator to control operation of the cannulation device 100. A smallest lateral dimension (e.g., length or width) of the display screen 108 may range from between about 0.5 inches and 3 inches in some embodiments, although larger display screens 100 are possible in various embodiments. In some embodiments images may be capable of being recorded, stored, and/or transmitted to a remote receiver.

The cannulation device 100 may further include a means to stabilize a hollow bore needle and/or syringe with a needle to cannulate a vascular access structure. Such a design of the cannulation device 100 may enable the ultrasound imager and needle to be held in one hand. For example, as illustrated in FIG. 1, a needle-positioning member 110 is coupled with the body 102, such as at a medial portion of the body 102 between the patient interface end 104 and the display end 106. The needle-positioning member 110 may be permanently or removably coupled with the body 102 in various embodiments. For example, a fastener and/or quick connect/disconnect mechanism (such as a clip) may be used to couple the needle-positioning member 110 with the body 102, which may enable the needle-positioning member 110 to be removed and replaced (e.g., may be disposable), while the body 102 (and ultrasound components) may be reused. In some embodiments, the needle-positioning member 110 may extend laterally outward from the body 102 at an angle, such as less than or about 90 degrees relative to a longitudinal axis of the body 102, with a distal end of the needle-positioning member 110 pointing substantially away from the display end 106. The distal end of the needle-positioning member 110 may include a needle holder 112 that may securely receive a cannulation needle 114 during the insertion process. For example, a tip of the cannulation needle 114 may be angled toward a point under the probe tip in some embodiments, such that when the probe tip is aligned with a target vascular access structure, the tip of the cannulation needle 114 is similarly aligned with the target vascular access structure. In some embodiments, the cannulation needle 114 may be stored in a retracted position and advanced from the protective sheath only when the cannulation needle 114 is being deployed.

In some embodiments, the needle-positioning member 110 may include an adjustment mechanism 116, such as (but not limited to) a ball joint, that may enable an angle of the needle holder 112 (and associated cannulation needle 114) to be adjusted relative to the body 102 and upper portion of the needle-positioning member 110. This may enable the angle of the cannulation needle 114 to be adjusted such that the cannulation needle 114 can be inserted over a range of insertion angles varying from 20-80 degrees relative to the surface of the skin and the body 102. The adjustment mechanism 116 may be positioned at any point of the needle-positioning member 110. For example, the adjustment mechanism 116 may be at the interface with the body 102, at the interface with the needle holder 112, and/or at a medial position along a length of the needle-positioning member 110.

In some embodiments, the cannulation needle 114 may be advanced using an electrical worm screw motor or equivalent to control for small forward and backward movements. In other embodiments, the cannulation needle 114 may be advanced manually through a conical or cylindrical locking system wherein a slight twist of the needle holder 112 will loosen or tighten the grip of the cannulation needle 114. Further, the distance of the tip of the cannulation needle 114 from a middle of the contact point of the ultrasound probe with the skin can vary in some embodiments from between 0.5 cm and 4 cm to facilitate stable and proper insertion of the cannulation needle 114 into the target vascular access structure. Both the angle of the cannulation needle 114 and distance from the tip of the cannulation needle 114 to the contact point of the ultrasound probe may be fixed and/or may be varied by the operator in various embodiments.

Once the vessels are imaged, for example with the cannulation device 100 being held by one of the operator's hands, the cannulation needle 114 may be advanced through the skin by the operator's other free hand and/or by a motorized delivery system. Once in the femoral artery (in this example) or other vascular access structure, a thin guidewire may be inserted through the hollow bore needle into the artery under visualization of the images displayed on display screen 106. At this point the entire cannulation device 100 may be lifted upward, leaving the guidewire inserted in the artery. In some embodiments, the needle-positioning member 110 and/or needle holder 112 may be disconnected from the body 102. The guidewire is then used to maintain vascular access and a vascular access sheath and dilator can be inserted into the blood vessel over the wire.

The novel approach to vascular access and device to facilitate vascular access and novel approach coupling image-guided transcutaneous arterial access for rapid placement of a REBOA catheter combined with Neuroprotective CPR provides a novel means to rapidly improve blood pressures, especially cerebral and coronary blood flow, during CPR.

Figure 2:
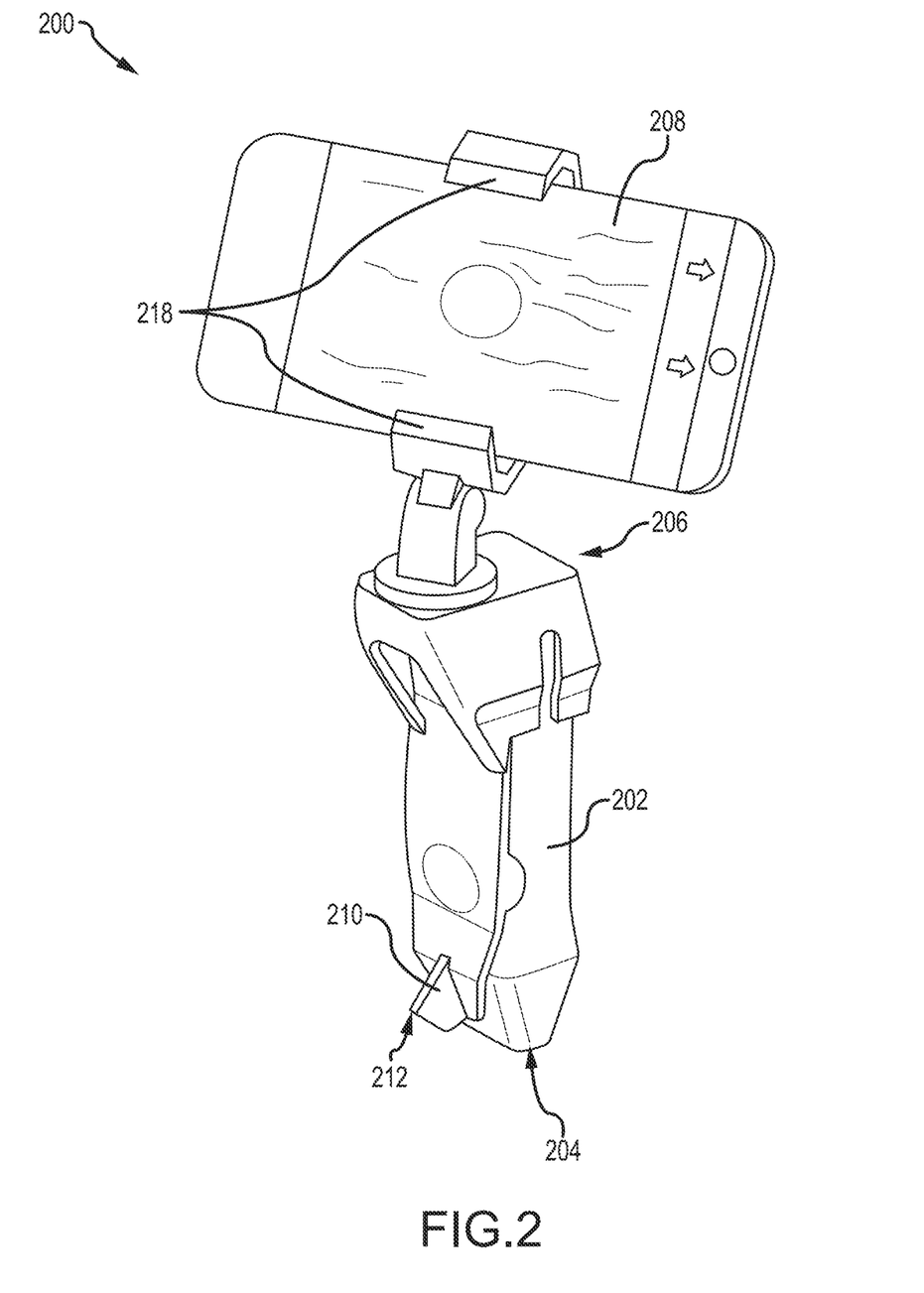
FIG. 2 illustrates a handheld cannulation device according to embodiments of the present technology.

FIG. 2 illustrates another embodiment of an ultrasound-guided cannulation device 200. The cannulation device 200 may be similar to cannulation device 100 and may include any feature described in relation to cannulation device 100. The cannulation device 200 may be a handheld device that may enable an operator to use ultrasound to visually locate and subsequently cannulate (or otherwise access) a desired vascular access structure. The cannulation device 200 may include an elongate body 202 that may be sized and shaped to be graspable using a single hand. The body 202 may include all necessary components to generate and view an ultrasound image. For example, the body 202 may house a battery or other power source, one or more processors, circuits, ultrasonic transducers, display screens, etc. In some embodiments, a total length of the body 202 may be between 4 inches and 15 inches, between 6 inches and 12 inches, or between 8 inches and 10 inches, although other lengths are possible. A total weight of the cannulation device 200 may be less than 5 pounds, less than 4 pounds, less than 3 pounds less than 2 pounds, or less.

A patient interface end 204 may be or include a probe tip that includes one or more ultrasonic transducers that may transmit high frequency sound waves (e.g., >20 kHz) to the body and record reflected or echo waves. An image processor disposed within the body 202 may use the recorded waves to develop 2-D real-time images. The image processor may also be disposed in other parts of the device. These images may be displayed, in real-time, using a display device 208 that is positioned on a display end 206 of the body 202. For example, in a particular embodiment, the display device 208 may be positioned on an opposite end surface as the patient interface end 204. The display device 208 may be integrated directed into the cannulation device 200 in some embodiments. In other embodiments, the display device 208 may be a detachable display (e.g., a portable monitor, tablet computer, mobile phone, etc.) that may be secured to the display end 206 using one or more clamps 218 and/or other connectors. The display screen may have any dimensions that permits the cannulation device 200 to be easily operable using a single hand. The display device 208 may be electrically coupled with the cannulation device 200 (e.g., to receive image data for display) via one or more wires or other electrical connectors. In some embodiments, the display device 208 may be wirelessly coupled to the cannulation device 200 (e.g., to receive image data for display), such as using Bluetooth, Wi-Fi, 5G, LTE, and/or other wireless communication protocol. The display 208 may be powered by a same or different power source as the rest of the cannulation device 200.

In some embodiments, the display device 208 may be adjustably coupled with the body 202. For example, the clamp 218 and/or other mount for the display device 208 may enable the display device 208 to be tilted and/or rotated relative to the body 202, which may enable the viewing angle of the display device 208 to be adjusted by a user.

The cannulation device 200 may further include a means to stabilize a hollow bore needle and/or syringe with a needle to cannulate a vascular access structure. Such a design of the cannulation device 200 may enable the ultrasound imager and needle to be held in one hand. For example, as illustrated in FIG. 2, a needle-positioning member 210 is coupled with the body 202, such as at a lower portion of the body 202 proximate the patient interface end 204. The needle-positioning member 210 may include a needle holder 212 that may securely receive a cannulation needle during the insertion process. The needle holder 212 may be a cylindrical channel defined through a length of the needle-positioning member 210 in some embodiments. For example, the channel may be angled toward a point under the probe tip in some embodiments, such that when the probe tip is aligned with a target vascular access structure, the tip of a cannulation needle inserted within the channel is similarly aligned with the target vascular access structure. The needle-positioning member 210 may be adjustable in some embodiments. For example, the needle-positioning member 210 may be pivoted relative to the body 202 to adjust an angle of the channel/needle holder 212 to adjust a needle insertion angle to an angle of between 20 degrees and 80 degrees in one or two axes relative to a horizontal plane. Such adjustability may enable the cannulation device 200 to be used to deliver an intra-aortic balloon to the femoral artery at different angles. Such adjustability may also enable the cannulation device 200 to be usable with other vascular structures and/or for different cannulation procedures. In some embodiments, a retractable and/or detachable needle-positioning member 210 may be used, which may enable the needle to be stabilized using the cannulation device 200 and allowing the rescuer to position the needle, advance the needle into the femoral artery under direct visualization. The needle-positioning member 210 may then enable a user to remove their hand from the needle to free the hand up for threading a flexible guidewire through the bore of the needle.

The angle and/or other position of the needle-positioning member 210 may be adjusted manually and/or automatically. For example, in some embodiments the angle of the needle holder may be automatically adjusted based upon the determination by the imaging system of the depth of the artery under study. In some embodiments, the needle may be automatically advanced under imaging by the imaging system and motorized needle insertion motor. In some embodiments, the distance from the needle holder to the imaging probe can be adjusted to facilitate both viewing of the needle as it is inserted, regardless of whether the operator views the artery in a cross-section, transverse-section and/or other imaging section.

In operation, a user may hold the body 202 with one hand while the other hand is used to cannulate the femoral artery using a syringe attached to a needle. The user may maneuver the probe over a patient's leg and view the display device 208 to locate the femoral artery (or other vascular access structure). The needle may be inserted through the needle holder 212 (which may occur prior to locating the vascular access structure) and inserted into the vascular access structure. The syringe may be removed and a guidewire may be advanced through a hollow bore of the needle and into the artery under ultrasound visualization. A sheath may be advanced over the guidewire and then the needle may be retracted into a sheath to protect the user from an inadvertent needle stick. In some embodiments, the needle-positioning member 210 may be detached from the body 202. A REBOA catheter may be placed into the femoral artery and advanced blindly to the level of the diaphragm. The cannulation device 200 may be easily rotated (and the display device 208 adjusted) to visualize the guidewire as it is advanced into the vessel. Such processes may enable intra-aortic balloons to be more easily and accurately positioned for REBOA procedures, even when used by out-of-hospital personnel.

Figure 3:
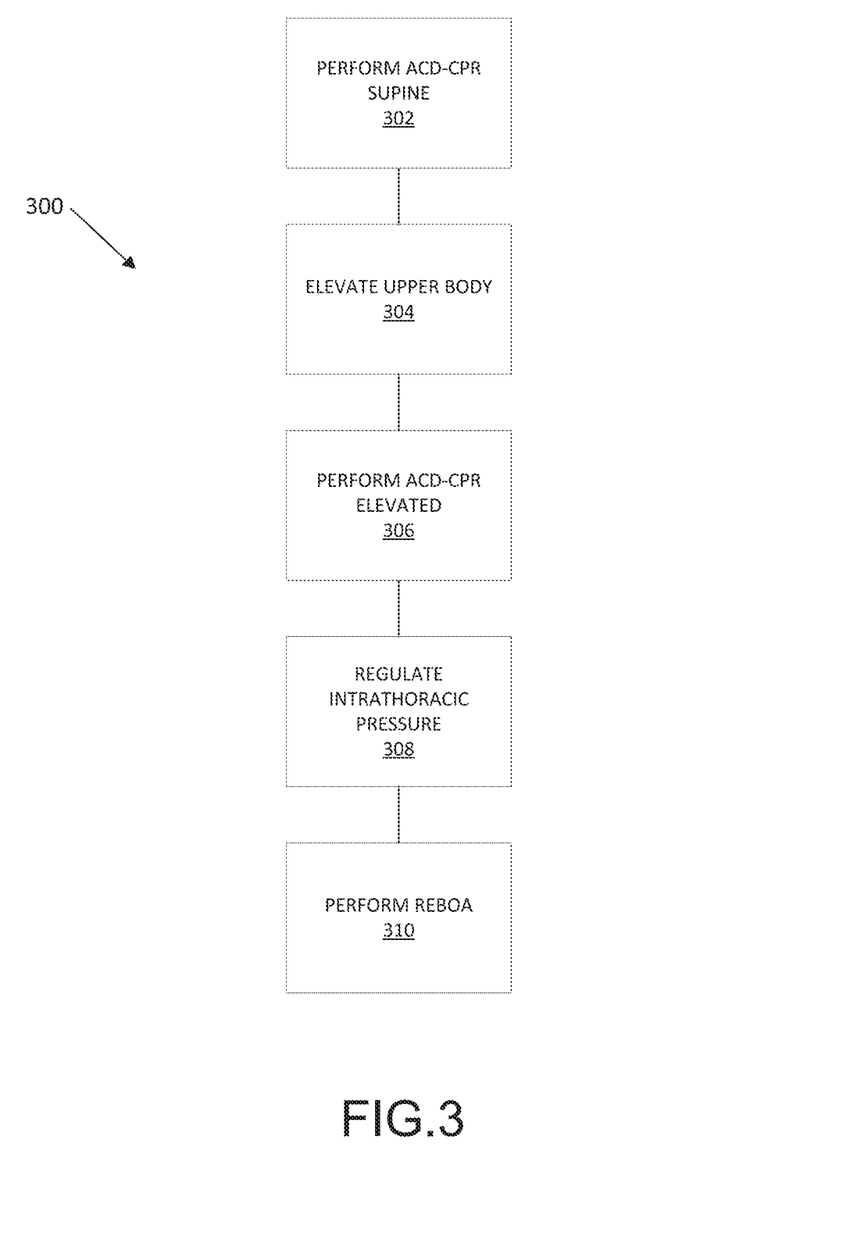
FIG. 3 illustrates operations of a method for performing Neuroprotective CPR in conjunction with REBOA according to embodiments of the present technology.

FIG. 3 depicts a process 300 for performing Neuroprotective CPR in conjunction with REBOA. Process 300 may be performed using a cannulation device such as those described herein. Process 300 may include performing active compression decompression cardiopulmonary resuscitation (ACD-CPR) on an individual while the individual is in a supine position in general alignment with a horizontal plane at operation 302. At operation 304, the individual's head, shoulders, and heart may be elevated relative to the individual's lower body while the individual's lower body remains generally aligned with the horizontal plane. The head may be elevated to a height of between about 10 cm and 30 cm above the horizontal plane and the heart may be elevated to a height of between about 5 cm to 15 cm or 8 cm and 12 cm above the horizontal plane. The individual's chest may be compressed and/or actively decompressed while the individual's head, shoulders, and heart are elevated at operation 306. In some embodiments, the elevation of the individual and/or the chest compressions/decompressions may be performed using a head up CPR elevation device, such as those described in U.S. application Ser. No. 17/668,266, U.S. application Ser. No. 17/335,922, U.S. application Ser. No. 17/222,476, U.S. application Ser. No. 16/955,382, U.S. application Ser. No. 16/201,339, U.S. Pat. Nos. 11,259,988, 11,246,794, 11,096,861, 11,020,314, 10,667,987, 10,406,069, 10,406,068, 10,350,137, 9,801,782, 9,750,661, 9,707,152, 10,092,481, and 10,245,209, the complete disclosures of which have previously been incorporated by reference for all intents and purposes.

At operation 308, the intrathoracic pressure of the individual may be regulated using an impedance threshold device interfaced with the individual's airway and/or other intrathoracic pressure regulation device both while the individual is in the supine position and while the individual's head, shoulders, and heart are elevated relative to the lower body. For example, the intrathoracic pressure regulation may be performed before commencement of chest compressions, during chest compressions, and/or after chest compressions. At operation 310, REBOA may be performed. For example, an intra-aortic balloon may be positioned within the patient's aorta to occlude blood flow from the aorta during the performance of CPR. The intra-aortic balloon may be positioned before commencement of chest compressions, during chest compressions, and/or after chest compressions.

Placement of the intra-aortic balloon may be performed using a cannulation device, such as cannulation device 100/200. For example, an operator may position the patient interface end 104/204 of the body 102/202 against the patient. The operator may use the images presented on display screen/device 108/208 to position the cannulation needle 114 in the femoral artery and may subsequently advance the cannulation needle 114 through the skin. A guidewire may then be inserted through the hollow bore needle into the artery under visualization of the images displayed on display screen/device 108/208. This guidewire may be used to advance the intra-aortic balloon to the aorta for subsequent inflation and occlusion of the aortic blood flow.

In some embodiments after there is a return of circulation to the individual, the REBOA balloon may remain inflated for a period of time (e.g., up to 5 minutes, up to 10 minutes, up to 15 minutes, up to 20 minutes, up to 25 minutes, up to 30 minutes, up to 45 minutes, or up to one hour in duration), depending upon the individual's physiologic status, for example, the individual's blood pressure. In some embodiments, the balloon deflation will occur based upon one or more physiologic measurements, such as a blood pressure of the individual. The physiologic measurements may be determined using one or more physiological sensors, such as (but not limited to) blood pressure sensors that are interfaced with the individual. The balloon may be deflated slowly or rapidly based upon the physiologic measurements. A closed loop or open loop feedback system may be used in some embodiments to control the timing and/or rate of balloon deflation after the return of spontaneous circulation.

In some embodiments, the deflation of the REBOA balloon may be coordinated with a change in elevation of the individual's head and thorax in order to maximize blood flow to the brain. In this case, blood flow to the brain may be monitored invasively and/or noninvasively. For example, the blood flow may be monitored based on a measurement of end tidal $CO_2$ or/and cerebral oximetry. In this manner, the inflated balloon may be deflated safely, and in a partial manner if needed, in order to better perfuse the heart, the brain, and the organ systems distal to the balloon occlusion. Once the balloon is totally deflated, the balloon may be removed.

EXAMPLES

In one example, Neuroprotective CPR was performed for 30 minutes in a pig. After 30 minutes a REBOA catheter was inserted into the femoral artery and the aorta was occluded at the level of the diaphragm. Cerebral perfusion pressures increased by over 20 mmHg. When the head and thorax of the pig were lowered so they were horizontal instead of elevated, this effect was markedly decreased. As such, the combination of REBOA and Neuroprotective CPR provide a novel and unexpectedly superior way to perfusion the brain with blood during CPR. This physiology is shown in a series of hemodynamic tracing from a representative pig study.

Arterial, venous, and intracranial pressures were measured with microelectronic tipped Millar catheters during Neuroprotective CPR, as previously described (Moore J C, Salverda B, Rojas-Salvador C, Lick M, Debaty G, Lurie K. Controlled sequential elevation of the head and thorax combined with active compression decompression cardiopulmonary resuscitation and an impedance threshold device improves neurological survival in a porcine model of cardiac arrest. Resuscitation. 2020a; 150-23-28 DOI: https://doi.org/10.1016/j.resuscitation.2020.09.030). These tracings are illustrated in FIG. 4.

Figure 4:
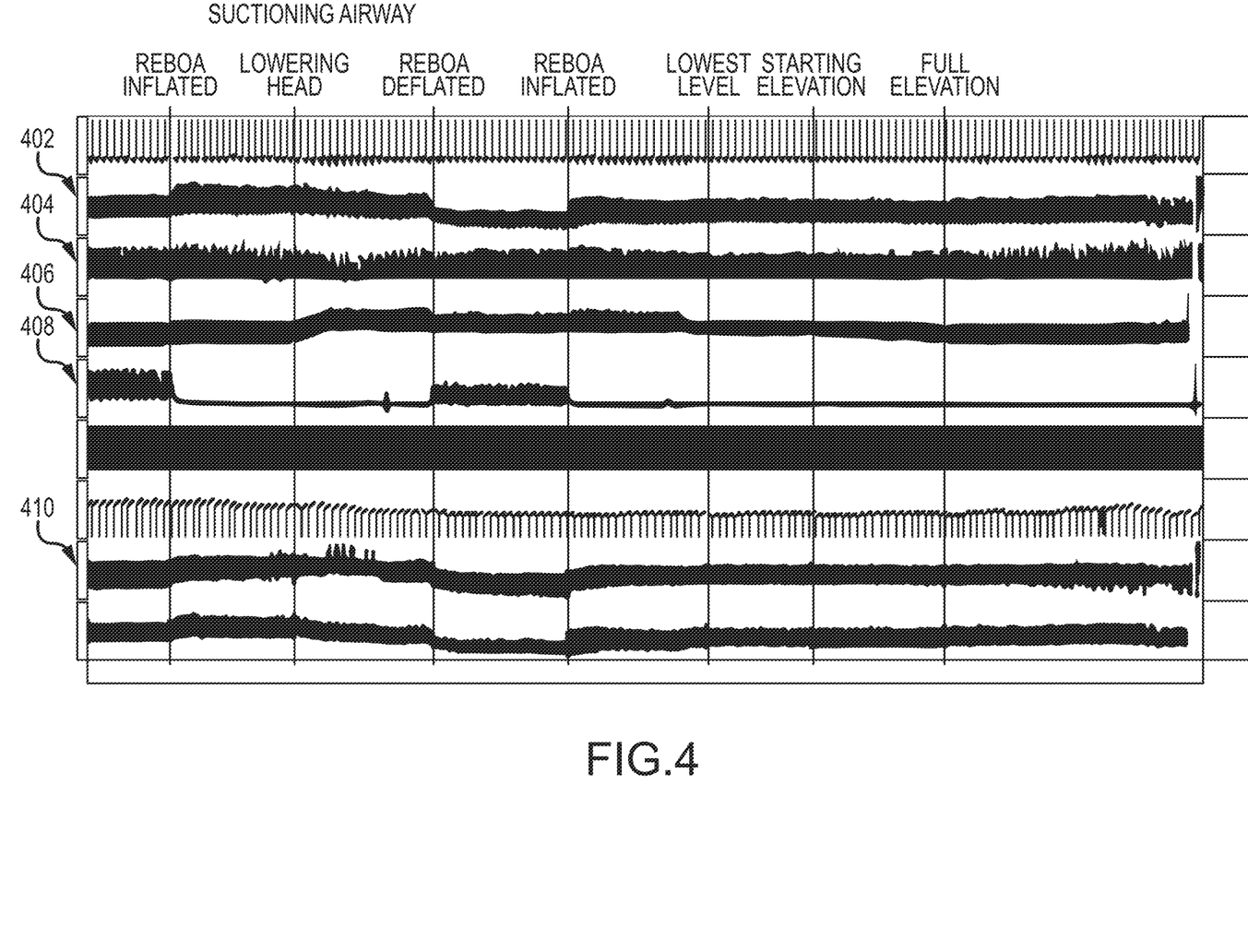
FIG. 4 illustrates tracings of physiological parameters during a pig study.

At the start of the tracings in FIG. 4, the pig had been receiving Neuroprotective CPR for 30 minutes. Before inflating the REBOA the arterial blood pressure was about 70/38 mmHg and the cerebral perfusion pressure was about 90/45 mmHg. After the REBOA inflation the arterial pressure increased to ~125/50 mmHg and the cerebral perfusion pressure increased to 100/45 mmHg. Upon lowering the head and thorax, arterial and cerebral perfusion pressures decreased abruptly and with deflation of the REBOA the arterial and cerebral perfusion pressures decreased to 50/20 mmHg and 40/0 mmHg, respectively. These tracings demonstrate the synergistic and surprise finding that REBOA+ Neuroprotective CPR can uniquely provide nearly normal arterial and cerebral perfusion pressures after prolonged Neuroprotective CPR, in the absence of any pharmacological intervention.

The Y axis on the right provides the unit of measurement of the physiological parameters. The Y axis on the left describes the parameter measured. The tracing 402 shows the aortic pressure, the tracing 404 shows the right atrial pressure, the tracing 406 shows the intracranial pressure, the tracing 408 shows the pressure in the distal aorta, and the tracing 410 shows the cerebral perfusion pressure. The x axis is time, in minutes.

Figure 5:
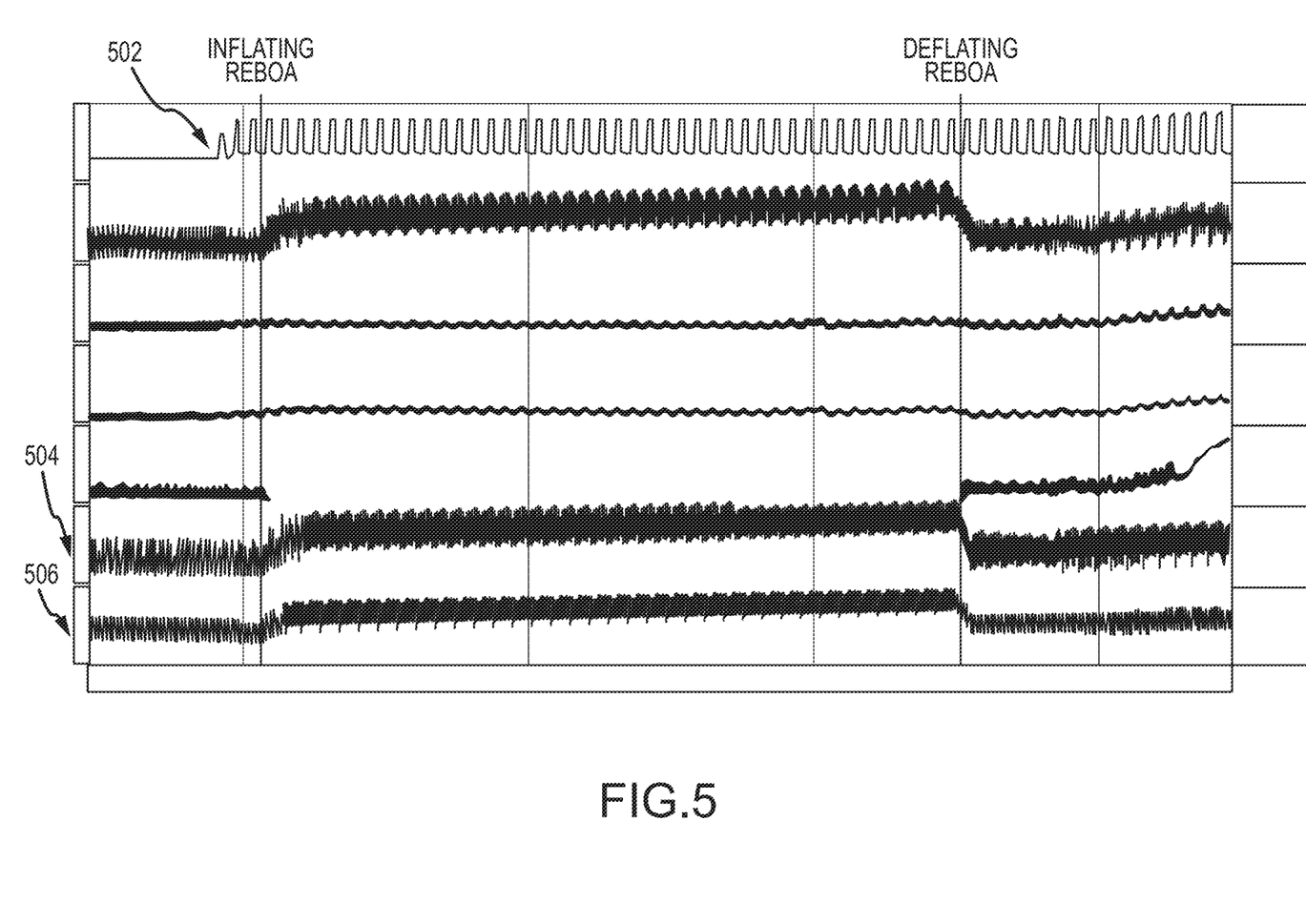
FIG. 5 illustrates tracings of physiological parameters during a pig study.

These findings are shown again in FIG. 5, from another similar pig study, where the impact of inflating the REBOA after 30 minutes of ongoing Neuroprotective CPR is shown in a higher resolution. The tracing 502 is the airway tracing. A positive pressure breath is delivered approximately 10 times per minute. The rise in aortic and cerebral pressures with REBOA during Neuroprotective CPR is profound. In FIG. 5, the rise in coronary (CorPP) (tracing 504) and cerebral (CerPP) (tracing 506) pressures with inflation of the REBOA during Neuroprotective CPR is clearly seen.

In another study, female and male swine (~40 kg) were sedated, intubated, and anesthetized. Bilateral femoral arterial access was obtained for continuous arterial pressure measurement and REBOA placement in the proximal thoracic aorta. Central venous and intracranial access was obtained for continuous measurement during CPR. Hemodynamics were measured with solid state pressure catheters. The arterial pressure catheter was placed in the thoracic aorta and confirmed via fluoroscopy. After 36 minutes of AHUP-CPR, animals underwent two-minute epochs of AHUP-CPR, AHUP+REBOA CPR, ACD+ITD CPR flat+REBOA, and ACD+ITD CPR flat. The reverse sequence was then performed. Pressures are reported as mean (mmHg)±standard deviation. A paired t-test was performed for the outcomes of Cerebral Perfusion Pressure (CerPP) and Coronary Perfusion Pressure (CorPP).

Figure 6:
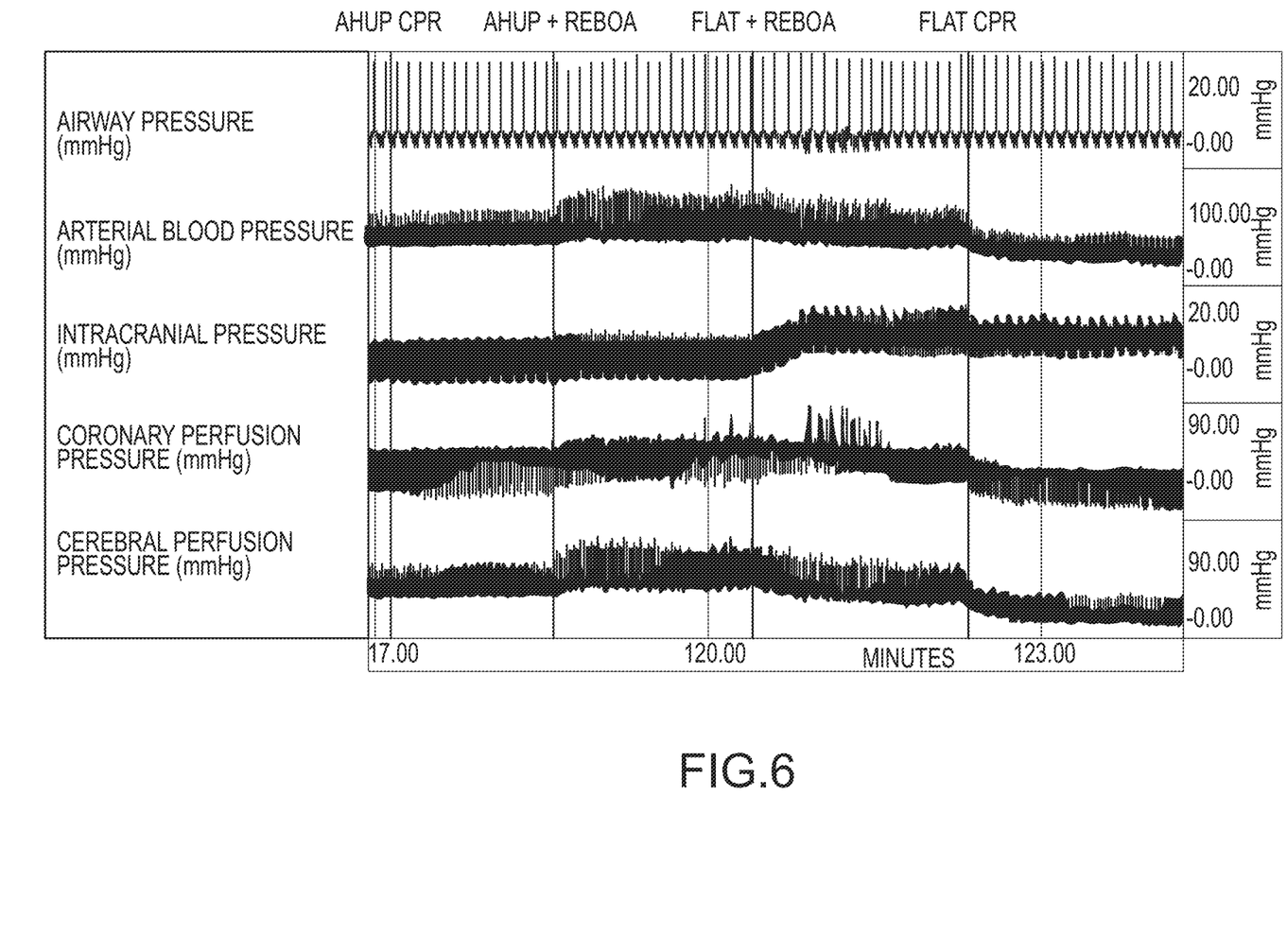
FIG. 6 illustrates tracings of physiological parameters during a pig study.

As illustrated in FIG. 6, the CerPP was 42.8±12.2 with AHUP+REBOA CerPP versus a CerPP with ACD+ITD CPR flat+REBOA of 25.9±11.5 (p<0.0001). The CorPP was 20.2±19.9 with AHUP+REBOA CorPP versus ACD+ITD CPR flat+REBOA CorPP of 15.7±18.8 (p<0.01). The AHUP+REBOA CerPP was 63% of the baseline CerPP value after 38 minutes of CPR. The return of Spontaneous Circulation (ROSC) was obtained in 4/7 (57%) after 50+ minutes of CPR.

Figure 7:
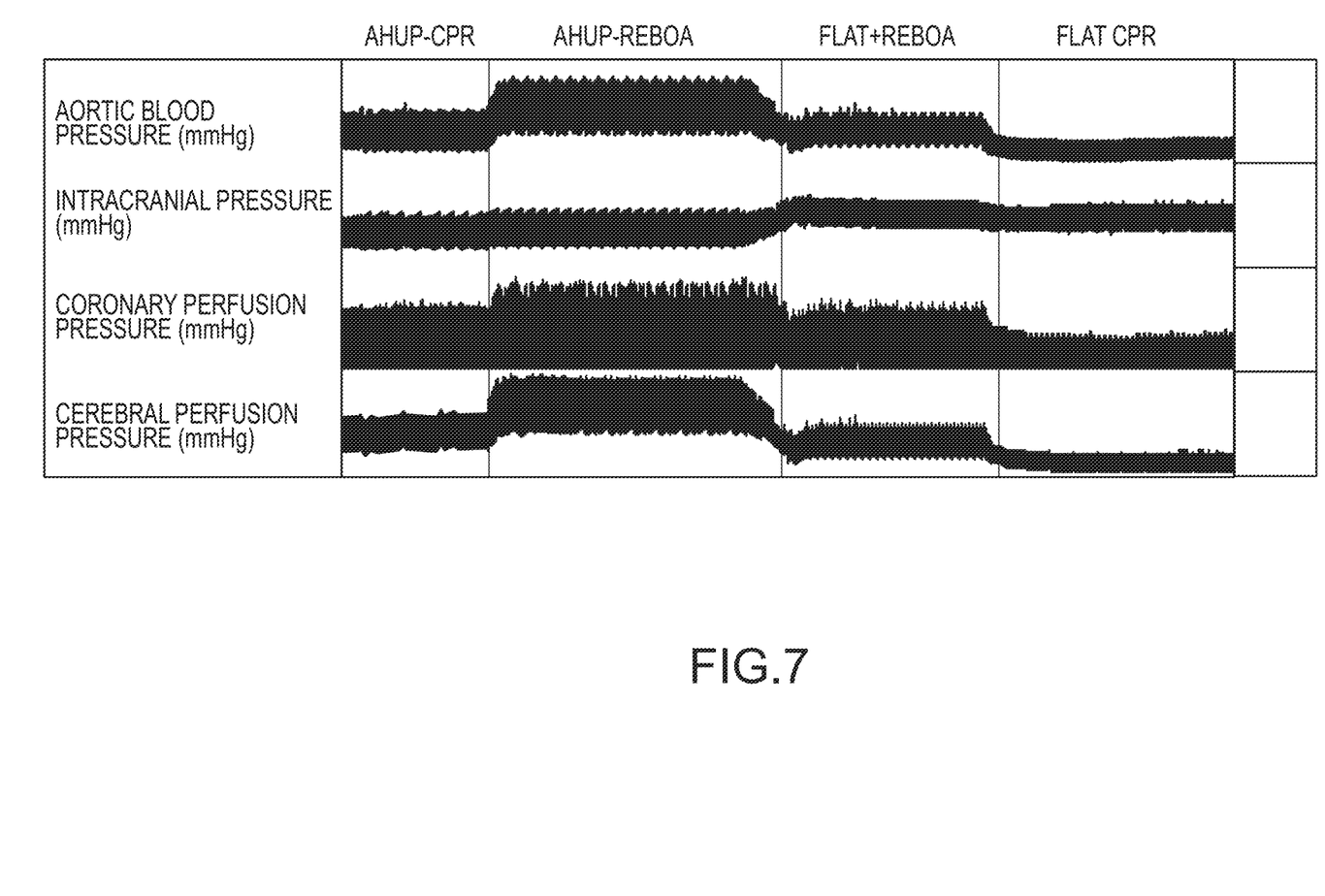
FIG. 7 illustrates tracings of physiological parameters during a pig study.

In another study, REBOA was added to the treatment of pigs (n=7) after 8 min of untreated VF and >40 min of AHUP-CPR, there was an immediate, profound, and unanticipated rise in coronary and most of all cerebral perfusion pressure, without a significant rise in ICP as shown in FIG. 7. All key hemodynamic parameters, especially cerebral perfusion pressure, increased immediately upon initiation of REBOA. By contrast, the benefits of REBOA were significantly less when the pigs were placed in the flat position. Statistically significant differences were observed only when REBOA was added to AHUP CPR (ACD+ITD in elevated position) and not when REBOA was added to ACD+ITD in the flat position.

In another study, a porcine model of untreated VF (15 min) was used to simulate refractory out-of-hospital cardiac arrest (r-OHCA). 22 pigs were randomized to either 25 min of AHUP-CPR (early AHUP) or 10 min of C-CPR followed by 15 min of AHUP-CPR (late AHUP) and then epinephrine, amiodarone, and defibrillation. Pigs in the early AHUP-CPR group had a 50% 24-hour survival rate and all survivors had normal pupillary reflexes. By contrast, with late AHUP-CPR only 1/10 pigs survived, and this animal remained comatose. Neurologic deficit scores were significantly better with early AHUP-CPR.

Figure 8:
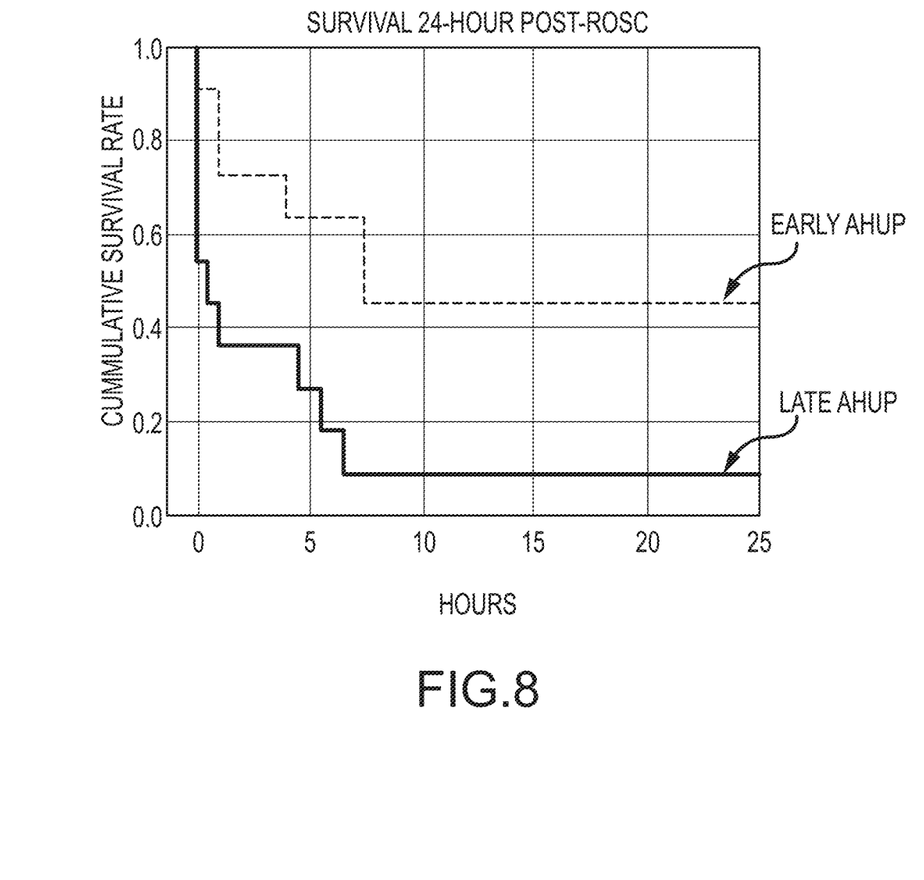
FIG. 8 illustrates a cumulative 24-hour survival rate during a pig study.

For the primary endpoint, 24-hour neurologic function, a veterinarian blinded to the CPR intervention assessed pigs using a Neurological Deficit Score (NDS, 0=normal and 260=worst deficit score or death). The cumulative 24-hour survival was 45.5% for early AHUP-CPR versus 9.1% for late AHUP-CPR (p<0.02) as shown in FIG. 8. The mean±SD NDS was 203±80 with early AHUP-CPR versus 259±3 with late AHUP-CPR group (p=0.04). Mean±SD ETCO2 (mmHg) values, known to correlate with circulation during CPR, were significantly higher with early versus late AHUP-CPR after 10 min of CPR (45±4 vs 27±6, p<0.001) and 24 min of CPR (42±9 vs 31±12, p<0.001). These findings are strongly supportive that the more rapid the restoration of circulation to the heart and brain after a prolonged arrest, the better the outcome.

These studies demonstrate that the combination of Neuroprotective CPR and REBOA may markedly improve brain perfusion during CPR by providing near normal cerebral perfusion pressures, higher brain blood flow, a higher likelihood of survival after cardiac arrest, higher compression and decompression phase arterial pressures proximal to the occlusion, and unexpectedly higher cerebral perfusion pressures. In particular, the examples have demonstrated increases of coronary and cerebral perfusion pressure of nearly 50%, which increases the effectiveness of head up CPR. In these studies, the femoral artery access was obtained with ultrasound guidance. In addition, these studies show the need for further interventions when pigs and patients cannot be resuscitated with just AHUP-CPR. There remains a great need for newer CPR techniques, methods and devices to further improve outcomes beyond which are shown in FIGS. 7 and 8.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations may be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the examples described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein and in the appended claims, the singular forms "a", "an", and "the" include plural references unless the context clearly dictates otherwise. Thus, for example, reference to "a heater" includes a plurality of such heaters, and reference to "the aperture" includes reference to one or more apertures and equivalents thereof known to those skilled in the art, and so forth.

Also, the words "comprise(s)", "comprising", "contain(s)", "containing", "include(s)", and "including", when used in this specification and in the following claims, are intended to specify the presence of stated features, integers, components, or operations, but they do not preclude the presence or addition of one or more other features, integers, components, operations, acts, or groups.

What is claimed is:

1. A method of performing cardiovascular resuscitation, comprising:
    elevating an individual's head, shoulders, and heart relative to the individual's lower body while the individual's lower body remains generally aligned with a horizontal plane;
    compressing the individual's chest while the individual's head, shoulders, and heart are elevated;
    regulating an intrathoracic pressure of the individual while the individual's head, shoulders, and heart are elevated relative to the lower body; and
    performing REBOA on the individual by positioning an intra-aortic balloon in the individual's aorta using an ultrasound-guided cannulation device and inflating the intra-aortic balloon.

2. The method of performing cardiovascular resuscitation of claim 1, further comprising:
    performing active compression decompression cardiopulmonary resuscitation on the individual while the individual is in a supine position in general alignment with the horizontal plane prior to elevating the individual's head, shoulders, and heart.

3. The method of performing cardiovascular resuscitation of claim 1, further comprising:
    actively decompressing the individual's chest between each chest compression.

4. The method of performing cardiovascular resuscitation of claim 1, wherein:
    regulating the intrathoracic pressure comprises interfacing an impedance threshold device with the individual's airway.

5. The method of performing cardiovascular resuscitation of claim 1, wherein:
    elevating the individual's head, shoulders, and heart comprises elevating the individuals' head to a height of between 10 cm and 30 cm above the horizontal plane and elevating the individual's heart to a height of between 5 cm to 15 cm above the horizontal plane.

6. The method of performing cardiovascular resuscitation of claim 1, wherein:
    REBOA is performed on the individual while the individual's head, shoulders, and heart are elevated.

7. The method of performing cardiovascular resuscitation of claim 1, wherein:
    positioning the intra-aortic balloon in the individual's aorta using the ultrasound-guided cannulation device comprises:
        locating a femoral artery of the individual using a display device of the ultrasound-guided cannulation device;
        inserting a needle into the femoral artery;
        advancing a guidewire into the femoral artery via a hollow bore of the needle; and
        advancing the intra-aortic balloon to the aorta using the guidewire.

8. The method of performing cardiovascular resuscitation of claim 1, further comprising:
    keeping the intra-aortic balloon in an inflated state for a predetermined period of time after a return of circulation to the individual.

9. The method of performing cardiovascular resuscitation of claim 8, wherein:
    the predetermined period of time is up to one hour.

10. The method of performing cardiovascular resuscitation of claim 1, further comprising:
    deflating the intra-aortic balloon after a return of circulation to the individual upon determining that a physiological measurement of the individual has reached a particular value.

11. The method of performing cardiovascular resuscitation of claim 10, wherein:
    the physiological measurement comprises a blood pressure of the individual.

12. The method of performing cardiovascular resuscitation of claim 1, further comprising:
    deflating the intra-aortic balloon after a return of circulation to the individual, wherein one or both of a timing and a rate of deflation is controlled using a closed loop feedback system with one or more physiologic measurements.

13. The method of performing cardiovascular resuscitation of claim 1, further comprising:
    deflating the intra-aortic balloon after a return of circulation to the individual, wherein one or both of a timing and a rate of deflation is controlled using an open loop feedback system with one or more physiologic measurements.

14. The method of performing cardiovascular resuscitation of claim 1, further comprising:
deflating the intra-aortic balloon after a return of circulation to the individual, wherein deflation of the intra-aortic balloon is coordinated with a change in elevation of the individual's head, shoulders, and heart.

15. The method of performing cardiovascular resuscitation of claim 14, wherein:
coordination of the deflation of the intra-aortic balloon is performed by monitoring blood flow to the individual's brain.

16. The method of performing cardiovascular resuscitation of claim 15, wherein:
monitoring blood flow to the individual's brain is performed using one or both of a measurement of end tidal $CO_2$ and a measurement of cerebral oximetry.

\* \* \* \* \*